US008637303B2

(12) United States Patent
Lapota et al.

(10) Patent No.: US 8,637,303 B2
(45) Date of Patent: *Jan. 28, 2014

(54) SYSTEM FOR MEASURING AND ANALYZING PROPERTIES OF WATER AND SEDIMENT SAMPLES

(75) Inventors: David Lapota, San Diego, CA (US); Bryan Travis Bjorndal, Carlsbad, CA (US); Gregory Wayne Anderson, San Diego, CA (US)

(73) Assignee: United States of America as represented by Secretary of the Navy, Washington, DC (US)

( * ) Notice: Subject to any disclaimer, the term of this patent is extended or adjusted under 35 U.S.C. 154(b) by 222 days.

This patent is subject to a terminal disclaimer.

(21) Appl. No.: 13/106,695

(22) Filed: May 12, 2011

(65) Prior Publication Data

US 2011/0223655 A1  Sep. 15, 2011

Related U.S. Application Data

(63) Continuation-in-part of application No. 11/641,343, filed on Dec. 19, 2006, now Pat. No. 7,964,391, which is a continuation-in-part of application No. 11/603,656, filed on Nov. 22, 2006, now Pat. No. 7,838,212, which is a continuation-in-part of application No. 11/586,747, filed on Oct. 10, 2006, now abandoned, and a continuation-in-part of application No. 11/586,745, filed on Oct. 10, 2006, now Pat. No. 7,704,731.

(51) Int. Cl.
*C12M 1/34* (2006.01)

(52) U.S. Cl.
USPC .................................. 435/288.7; 435/286.7

(58) Field of Classification Search
USPC ............................................ 435/288.7, 286.7
See application file for complete search history.

(56) References Cited

U.S. PATENT DOCUMENTS

| 4,774,055 A | 9/1988 | Wakatake et al. |
| 4,950,594 A | 8/1990 | Stiffey |
| 5,565,360 A | 10/1996 | Lapota et al. |

(Continued)

OTHER PUBLICATIONS

Cussatlegras et al., "Bioluminescence of the dinoflagellate *Pyrocystic noctiluca* induced by laminar and turbulent Couette flow", 2004, Journal of Experimental Marine Biology and Ecology, 310, pp. 227-246.*

(Continued)

*Primary Examiner* — Jonathan Hurst
(74) *Attorney, Agent, or Firm* — Kyle Eppele; J. Eric Anderson

(57) ABSTRACT

A system for assessing the characteristics and toxicity of a water sample comprising: a test chamber; an optical signal generator configured to emit an optical signal into the test chamber; a first digital filter disposed between the optical signal generator and the test chamber; a first optical transducer disposed to generate a first data signal in response to detecting radiant energy in the test chamber; a second digital filter disposed between the first optical transducer and the test chamber; an aqueous suspension of dinoflagellates contained within the test chamber and mixed with the water sample; a stimulator disposed to stimulate the dinoflagellates to emit a bioluminescence signal; and a microprocessor operatively coupled to the optical signal generator, the first digital optical filter, the stimulator, the first optical transducer, and the second digital filter, wherein the microprocessor is configured to assess the spectral characteristics and toxicity of the water sample.

20 Claims, 18 Drawing Sheets

(56) References Cited

U.S. PATENT DOCUMENTS

| | | | |
|---|---|---|---|
| 5,840,572 | A | 11/1998 | Copeland et al. |
| 6,133,021 | A | 10/2000 | Gu et al. |
| 7,182,912 | B2 | 2/2007 | Carey et al. |
| 7,364,698 | B2 | 4/2008 | Fujita et al. |
| 7,692,784 | B2 * | 4/2010 | MacKinnon et al. ......... 356/300 |
| 7,704,731 | B2 | 4/2010 | Bjorndal et al. |
| 7,705,339 | B2 * | 4/2010 | Smith et al. .................... 250/576 |
| 7,838,212 | B2 | 11/2010 | Bjorndal et al. |
| 2008/0085506 | A1 | 4/2008 | Bjorndal et al. |

OTHER PUBLICATIONS

Robert W. Sabate, Arthur V. Stiffey, and Edmund L. Dewailly; Bioluminesence in Toxicity Testing; 46 Environmental Geosciences, vol. 2, No. 1, pp. 46-53; 1995.

B. M. Sweeney, F. T. Haxo, and J. W. Hastings; Action Spectra for Two Effects of Light on Luminescence in Gonyaulax polyedra; The Journal of General Physiology; Nov. 1, 1959, vol. 43, pp. 285-299.

J. Woodland Hastings and Beatrice M. Sweeney; On the Mechanism of Temperature Independence in a Biological Clock; Proc. N. A. S.; Jul. 14, 1957, vol. 43, pp. 804-811.

* cited by examiner

SYSTEM FOR MEASURING AND ANALYZING PROPERTIES OF WATER AND SEDIMENT SAMPLES

CROSS-REFERENCE TO RELATED APPLICATIONS

This application is a continuation-in-part of U.S. Pat. No. 7,964,391, application Ser. No. 11/641,343, filed 19 Dec. 2006, entitled "Automated, Field-Portable System for Conducting Toxicity Measurements in Water, Soils, and Sediments" (Navy Case 98124), which is a continuation-in-part of U.S. Pat. No. 7,838,212, application Ser. No. 11/603,656, filed 22 Nov. 2006, entitled "Apparatus and Method for Providing Live Dinoflagellates for Toxicity Tests" (Navy Case #98123), which is a continuation-in-part of both U.S. application Ser. No. 11/586,747, filed 10 Oct. 2006, now abandoned, entitled "Method for Stimulation of Bioluminescent Organisms Via Turbulence Created by Gas Bubbles" (Navy Case #98122); and U.S. Pat. No. 7,704,731, application Ser. No. 11/586,745, filed 10 Oct. 2006, entitled "System and Method for Quantifying Toxicity in Water, Soil, and Sediments" (Navy Case #98125).

FEDERALLY-SPONSORED RESEARCH AND DEVELOPMENT

This invention was developed with federal funds and is assigned to the United States Government. Licensing and technical inquiries may be directed to the Office of Patent Counsel, Space and Naval Warfare Systems Center, Pacific, Code 72120, San Diego, Calif., 92152; voice (619) 553-5118; ssc_pac_t2@navy.mil. Reference Navy Case Number 101145.

BACKGROUND OF THE INVENTION

Current systems for analyzing the properties, and/or determining the toxicity, of soils, sediments, and water tend to be complex, time consuming, and require the skill of a technician in a laboratory. As a result, current toxicity tests can be expensive, and prone to user error. A need exists for an easier, less expensive, quicker, more accurate, field-portable system for measuring and analyzing the properties of water and sediment samples.

BRIEF DESCRIPTION OF THE DRAWINGS

Throughout the several views, like elements are referenced using like references. Figures are not drawn to scale.

DETAILED DESCRIPTION OF EMBODIMENTS

Figure 1:
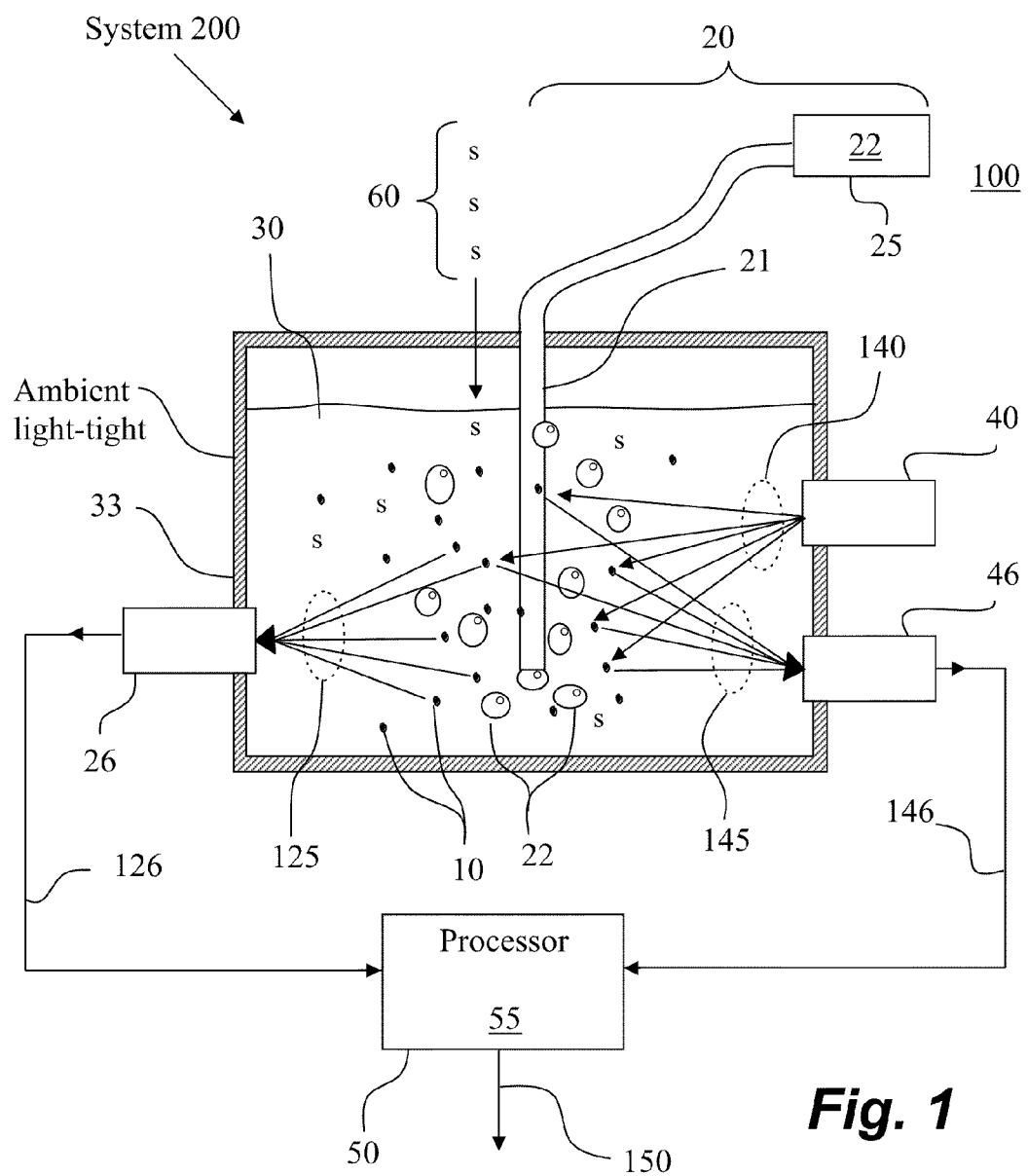
FIG. 1 shows an embodiment of a system for testing the toxicity of a test sample.

FIG. 1 shows a toxicity test system 200, a field-portable system for determining the toxicity of a test sample 60, such as water, soil and/or sediment. FIG. 1 shows how the test sample 60 may be added to an aqueous suspension 30 of dinoflagellates 10, which all may be contained in a test chamber 33. Inside the test chamber 33, if the dinoflagellates 10 are alive, the dinoflagellates 10 may be excited to fluoresce by an excitation signal 140 generated by an optical signal generator 40. The fluoresce signal 145 emitted by the excited dinoflagellates 10 may be detected by a first optical transducer 46 that is configured to produce a first data signal 146 in response to detecting the fluorescence signal 145. The first data signal 146 may be sent to a processor 50 where the first data signal 146 may be compared to control data 55. The dinoflagellates 10, inside the test chamber 33, may also be stimulated by a gas 22 to emit a bioluminescence signal 125 if the dinoflagellates 10 are alive. The gas 22 may be introduced into the aqueous suspension 30 of dinoflagellates 10 by a stimulator 20 in such a way as to create pressure pulses in the aqueous suspension 30 that cause the dinoflagellates 10 to bioluminesce. The bioluminescence signal 125 may be detected by a second optical transducer 26 that is configured to produce a second data signal 126 in response to detecting the bioluminescence signal 125. The second data signal 126 may be sent to the processor 50 where the second data signal 125 may be compared with the control data 55. The second data signal 126 may also be correlated with the first data signal 146, as discussed below. Based on the first and second data signals 146 and 126, the processor may generate an output 150 representing the toxicity of the test sample 60.

The dinoflagellates 10 in aqueous suspension 30 may be any species of dinoflagellates that fluoresce in response to a stimuli and bioluminesce in response to shear-stress inducing pressure pulses. Example embodiments of dinoflagellates 10 include, but are not limited to, *Gonyaulax polyedra, Pyrocystis lunula, Pyrocystis fusiformis*, and *Pyrodinium bahamense*. These species may be maintained, prior to testing, in an enriched seawater medium according to American Society for Testing and Materials Standard Guide for Conducting Static 96-h Toxicity Tests with Microalgae (ASTM 1990). Any number of dinoflagellate cells 10 may be added to aqueous suspension 30 provided their bioluminescence and fluorescence responses are measurable. By way of example, the population density of dinoflagellates 10 may be in the range of about 1 to about 500 dinoflagellate cells per milliliter of aqueous suspension 30. For example, about 3 milliliters of aqueous suspension 30 may comprise about 600 dinoflagellates 10. In another example, about 3 milliliters of aqueous suspension 30 may comprise about 300 dinoflagellates 10.

FIG. 1 also shows that the test chamber 33 may be light tight such that most ambient light may not enter the test chamber 33. The optical signal generator 40, the first optical transducer 46, the stimulator 20, and the second optical transducer 26 may be operatively coupled to the test chamber 33 in such a way as to allow them to perform their respective functions while preventing most ambient light from entering the test chamber 33.

The optical signal generator 40 is configured to generate an excitation signal 140 for exciting the dinoflagellates 10 to emit a fluorescence signal 145. Example embodiments of the optical signal generator 40 include, but are not limited to, a laser, a light emitting diode (LED), and any other optical signal generator capable of stimulating dinoflagellates 10 to emit fluorescence signal 145. The excitation signal 140 may be any signal capable of exciting the dinoflagellates 10 to emit a fluorescence signal 145. In one embodiment, the excitation signal 140 may be a continuous, blue, optical signal with a wavelength in the range of about 420 to about 440 nanometers configured to propagate into the test chamber 33 exciting dinoflagellates 10 to emit a fluorescence signal 145 with a wavelength of about 663 nanometers.

The first optical transducer 46 may be operatively coupled to the test chamber 33 and configured to detect the fluorescence signal 145 from excited dinoflagellates 10 in the test chamber 33. In response to detecting the fluorescence signal 145, the first optical transducer 46 may then generate the first data signal 146, an electrical signal, which is representative of a characteristic of interest of the fluorescence signal 145. Characteristics of interest of the fluorescence signal 145 include, but are not limited to, intensity, duration, wavelength, and photon count. Example embodiments of the first optical transducer 46 include, but are not limited to, a photomultiplier tube, a photodiode, a charge-coupled device (CCD), and any other device capable of generating a first data signal 146 in response to detecting the fluorescence signal 145.

The stimulator 20 may be operatively coupled to the test chamber 33 such that the stimulator 20 is configured to stimulate the dinoflagellates 10 in the test chamber 33 to emit bioluminescence signal 125. The stimulator 20 may be any device capable of introducing gas 22 into aqueous suspension 30 in such a way as to create turbulence in the aqueous suspension 30 such that the dinoflagellates 10 are stimulated to emit the bioluminescent signal 125. Pressure pulses caused by the turbulence of gas 22 moving through aqueous suspension 30 may cause the dinoflagellates 10 to bioluminesce. As shown in FIG. 1, the stimulator 20 may comprise a gas source 25 and a gas tube 21 for introducing the gas 22 into the aqueous suspension 30. The gas source 25 may be a gas reservoir, a gas pump, or any source capable of providing gas 22. The gas tube 21 may be a tube, a nozzle, a pipe, or any other device capable of transporting gas 22 from the gas source 25 and introducing gas 22 into aqueous suspension 30. Suitable gases for the gas 22 include, but are not limited to, air, nitrogen, oxygen, carbon dioxide, or any other gas that is capable of inducing bioluminescence through turbulence. For example, in one embodiment, the gas 22 may be air and the gas source 25 may be an air pump that pumps air 22 from the surrounding environment 100 into aqueous suspension 30.

Introducing gas 22 into aqueous suspension 30 creates turbulence, which induces fluid shear stress in aqueous suspension 30, which serves to stimulate the dinoflagellates 10 to emit bioluminescence signal 125. The wavelength of the bioluminescence signal 125 will generally lie within the range of about 450 to about 500 nanometers. Fluid shear stress may be defined as a change in direction or pressure of the fluid surrounding the dinoflagellates 10. In one embodiment, turbulence may be created when the ratio X/V ranges from about 0.667 to about 6.667, where X equals the flow rate of gas 22 into the aqueous suspension 30, and V equals the volume of aqueous suspension 30. For example, in one embodiment, the volume of aqueous suspension 30 may be 3 milliliters and the flow rate of gas 22 into aqueous suspension 30 may be 7 milliliters per second.

The second optical transducer 26 is operatively coupled to the test chamber 33 such that the second optical transducer 26 is capable of detecting the bioluminescence signal 125 from excited dinoflagellates 10 in the test chamber 33, as shown in FIG. 1. In response to detecting the bioluminescence signal 125, the second optical transducer 26 may then generate the second data signal 126, which is representative of a characteristic of interest of the bioluminescence signal 125. Characteristics of interest of the bioluminescence signal 125 include, but are not limited to, intensity, duration, wavelength, and photon count. The second optical transducer 26 may be any device capable of generating the second data signal 126 in response to the bioluminescence signal 125. Example embodiments of the second optical transducer 26 include, but are not limited to, a photomultiplier tube, a photodiode, a CCD, and any other device capable of generating a bioluminescence data signal 126 in response to detecting the second signal 125.

The processor 50 may be any device capable of receiving and transforming the second data signal 126 and the first data signal 146 into an output 150, which represents the toxicity of the test sample 60. Transforming the second data signal 126 and the first data signal 146 into an output 150 may be accomplished by measuring the first and second data signals 146 and 126 against control data 55 or a known fluorescence and bioluminescence standard. Mean relative fluorescence, standard deviation, and the coefficient of variation may be calculated by the processor 50 for the aqueous suspension 30 of dinoflagellates 10 in the test chamber 33. Relative fluorescence, calculated as a percentage of control values, can be plotted over time during the test. Example embodiments of the processor 50 include, but are not limited to, a computer, and any other device capable of correlating the second data signal 126 and the first data signal 146 and generating an output 150 that represents the toxicity of the test sample 60. The output 150 may be any audio, visual, or tactile output capable of communicating to a user the toxicity of the test sample 60. Although FIG. 1 shows the output 150 as exiting the processor 50, it is to be understood that the output 150 may also be used as an input to an internal function of the processor 50, or used as an input to another device or system.

The processor 50 may also control the sequence of testing. For example, after the aqueous suspension 30 has been placed in the test chamber 33, the processor 50 may turn on the optical signal generator 40 to emit the excitation signal 140 for y seconds (where y is an integer). During the emission of excitation signal 140 the processor 50 may record the first data signal 146 generated by the first optical transducer 46 in response to detecting fluorescence signal 145. After y seconds, the optical signal generator 40 may be turned off and the stimulator 20 may be activated by the processor 50 to stimulate the dinoflagellates 10 to emit a bioluminescence signal 125. Once the stimulator 20 has introduced gas 22 into the aqueous suspension 30, the processor 50 may record the second data signal 126 generated by the second optical transducer 26 in response to detecting the bioluminescence signal 125 emitted by stimulated dinoflagellates 10. The fluorescence data signal 146 and the bioluminescence data signal 126 may be compared to previous test results or to control data 55 stored in a look-up-table stored in the processor 50 in order to generate the output 150.

Figure 2:
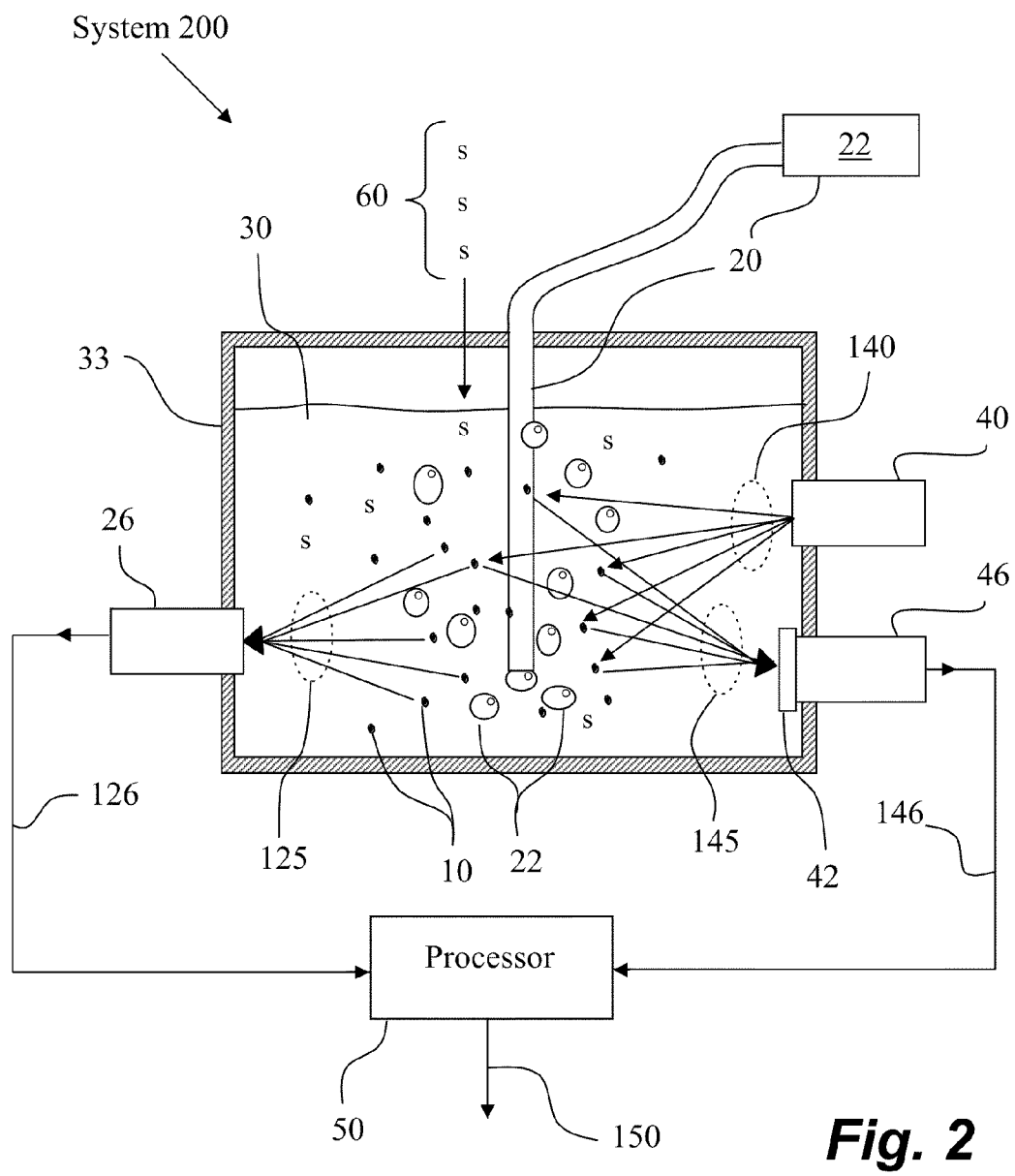
FIG. 2 shows a toxicity test system with a red optical filter.

FIG. 2 shows an embodiment of the toxicity test system 200 including a red optical filter 42 optically coupled between the dinoflagellates 10 and the first optical transducer 46. The red optical filter 42 may be any optical filter capable of preventing the excitation signal 140 from being detected by the first optical transducer 46 while allowing the fluorescence signal 145 to be transmitted through the red optical filter 42 to the first optical transducer 46. For example, the red optical filter 42 may be a wavelength-selective filter that only allows passage of optical signals falling within the range of about 660-690 nanometers.

Figure 3:
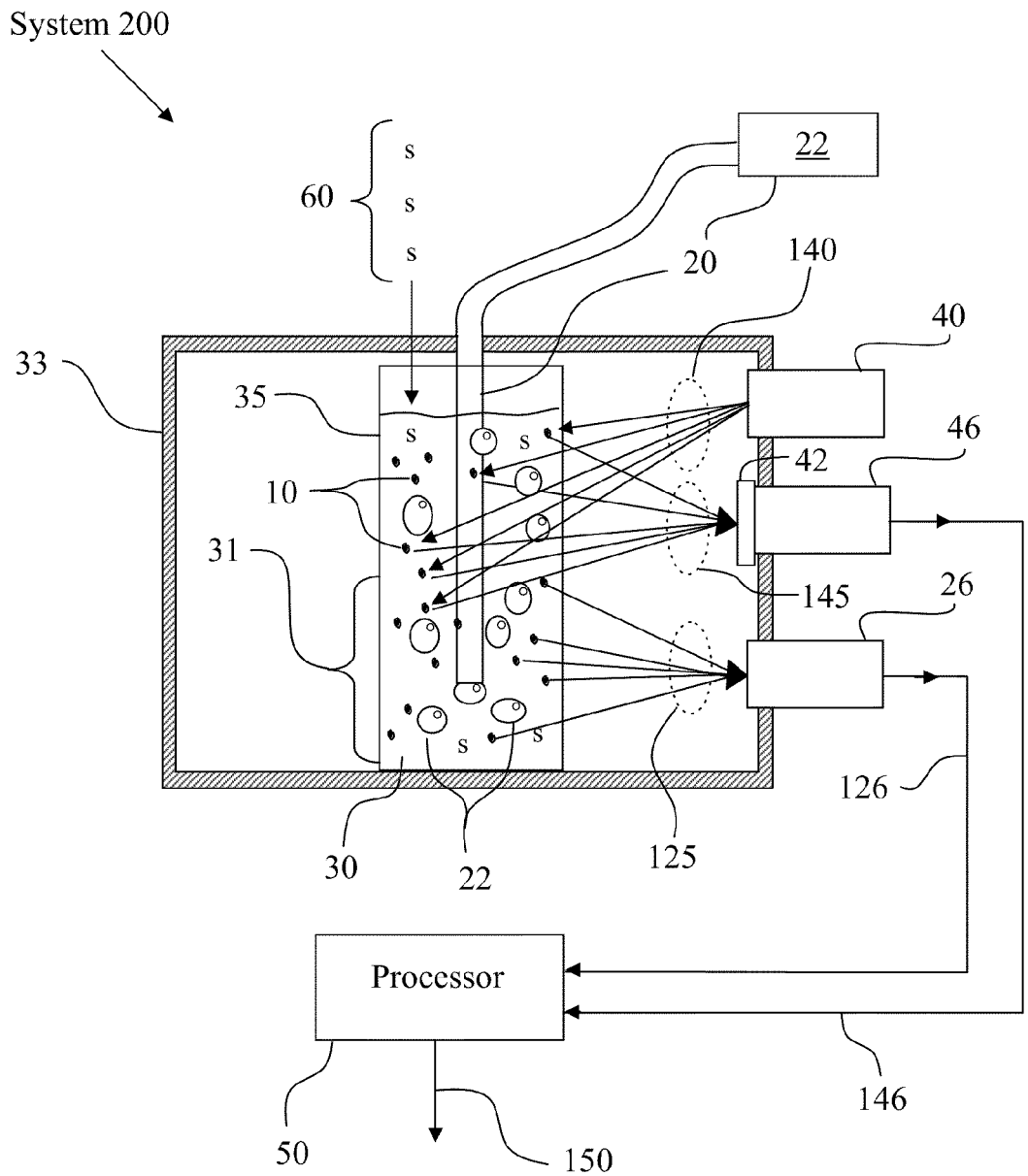
FIG. 3 shows a toxicity test system with a transparent sample container.

FIG. 3 illustrates another embodiment of system 200 where the aqueous suspension 30 and the test sample 60 may be contained in a removable, sample container 35. The sample container 35 is configured to be inserted into the test chamber 33. By way of example, the sample container 35 may be a test tube, a cuvette, or any other container capable of fitting inside the test chamber 33 and containing aqueous suspension 30. The sample container 35 may be made of polystyrene, glass, polycarbonate, or any other material that is optically transparent to the wavelengths of the excitation signal 140, the fluorescence signal 145, and the bioluminescence signal 125. The sample container 35 may be made of a material which is chemically non-reactive with sea water, as for example, glass, DELRIN®, polycarbonate, or polystyrene. The size and shape of the sample container 35 are limited only by the size and shape of the test chamber 33. The lower half of the sample container 35 may be defined as a lower end 31 into which the gas 22 may be introduced, as shown in FIG. 3.

Figure 4:
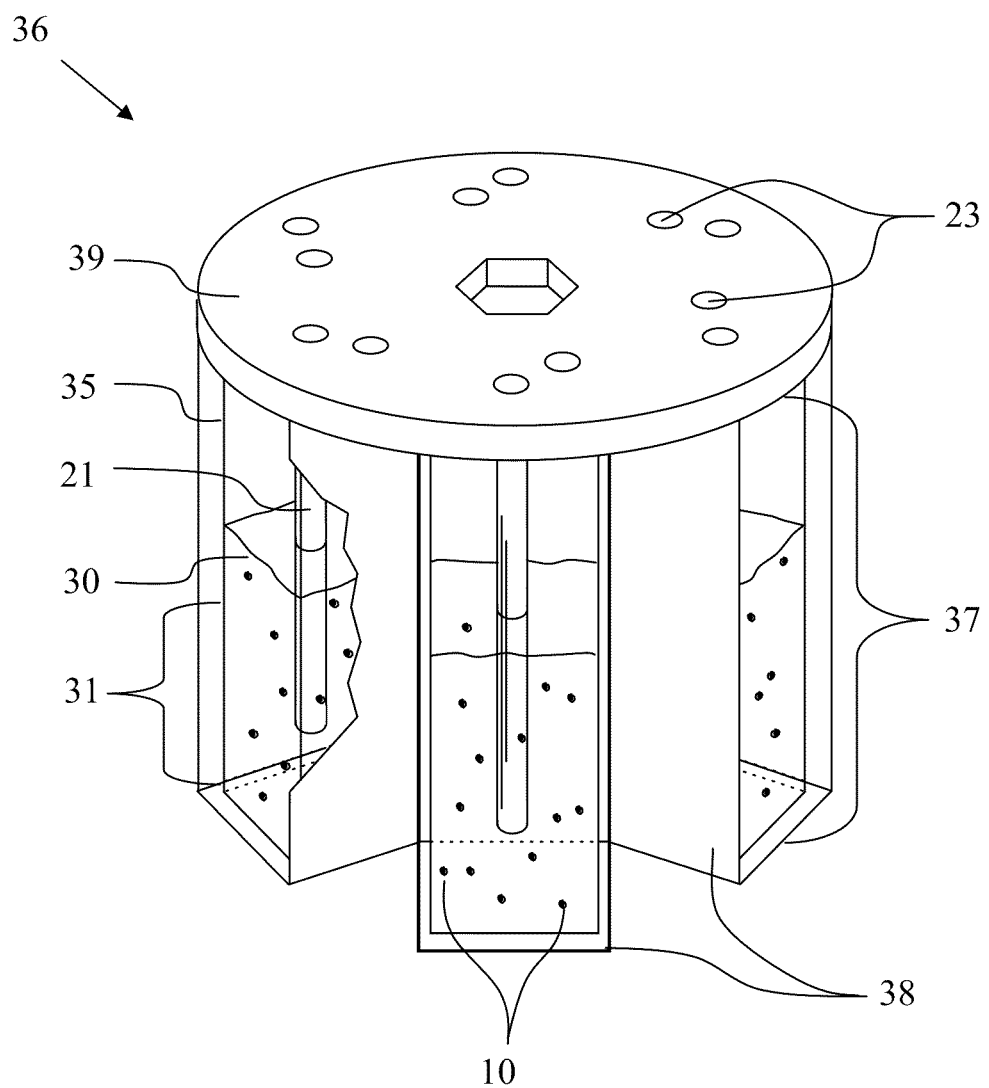
FIG. 4 shows a toxicity-test-system-compatible cartridge.

FIG. 4 shows a cartridge 36 that is configured to be supported inside the test chamber 33. The cartridge 36 comprises an array of sample containers 35. Each of the sample containers 35 contains a generally equal amount of the aqueous suspension 30 of dinoflagellates 10. As shown in FIG. 4, all of the sample containers 35 are optically isolated from each other by an array of optical isolation silos 38. Each optical isolation silo 38 comprises an optical window 37 through which the excitation signal 140, the fluorescence signal 145 and the bioluminescence signal 125 may pass. The cartridge 36 also comprises a cartridge cover 39 configured to cover each of the sample containers 35. In one embodiment, the cartridge cover 39 may comprise a vent 23 and a gas tube 21 for each of the sample containers 35. Each gas tube 21 extends into the lower end 31 of each sample container 35.

Figure 5:
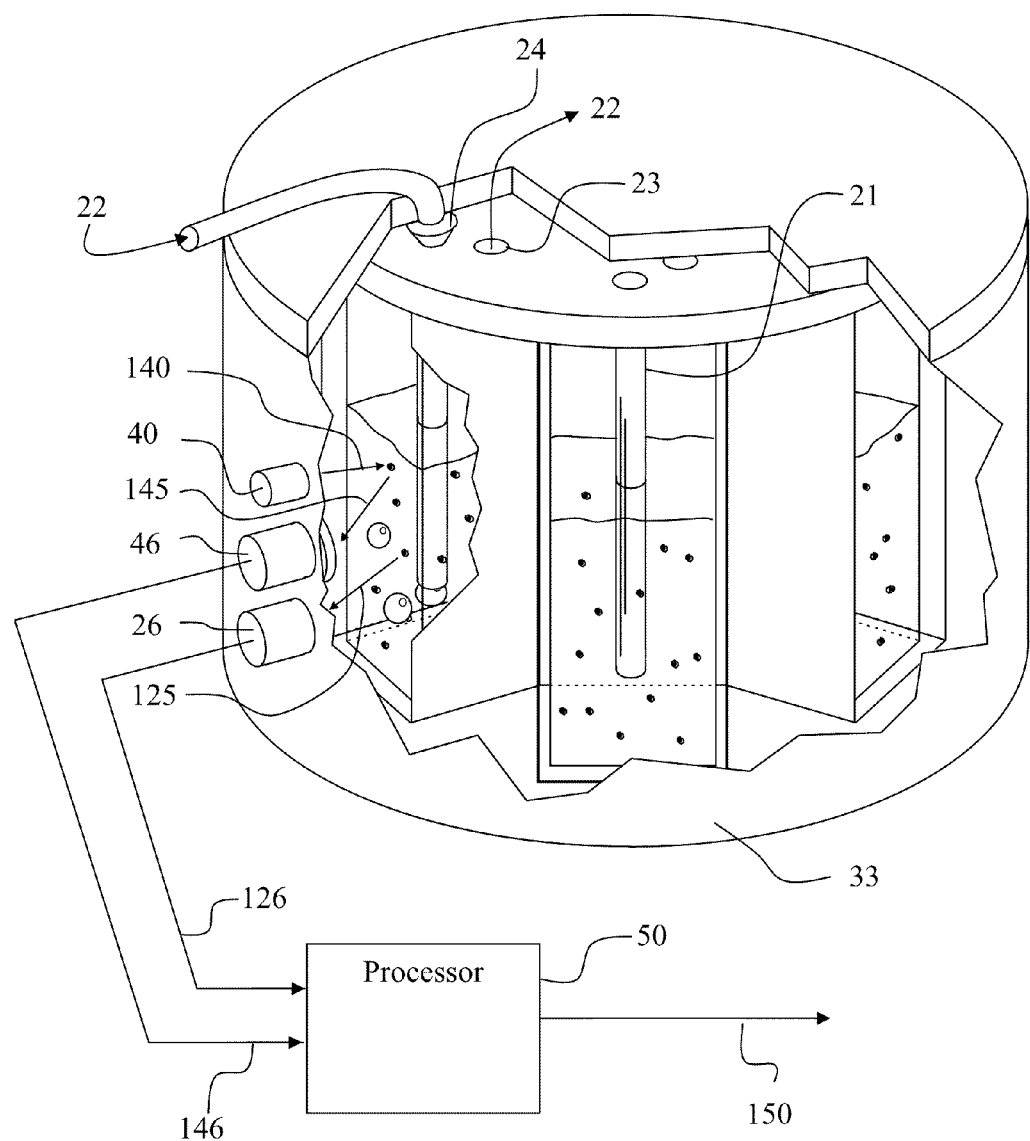
FIG. 5 is a perspective view of a cartridge in a test chamber.

FIG. 5 shows how the cartridge 36 may be operatively coupled to the toxicity test system 200 so that the gas 22 may be directed through the gas tube 21 into the aqueous suspension 30 in the lower end 31 of each of the sample containers 35. The gas vent 23 is configured to allow the gas 22 to escape from each of the sample containers 35. FIG. 5 also shows a first coupling nib 24 that is configured to direct the gas 22 from the gas source 25 to pass into the gas tube 21 of the sample container 35 with which the first coupling nib 24 is aligned. The first coupling nib 24 may be any device or structure that allows gas 22 from the gas source 25 to be directed into the gas tube 21 with which the first coupling nib 24 is aligned.

Figure 6:
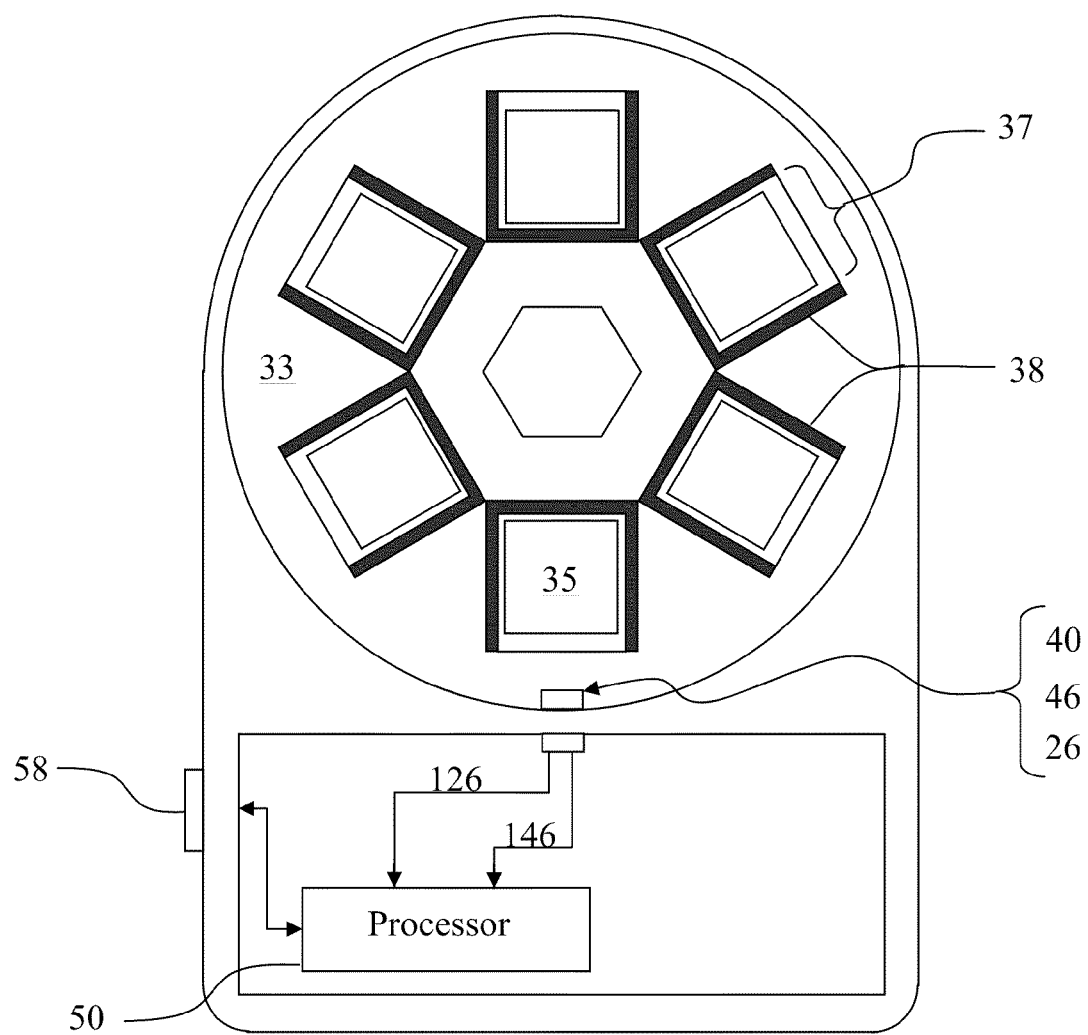
FIG. 6 is a top view of a cartridge in a test chamber.

FIG. 6 shows how each optical window 37 may be oriented on each optical isolation silo 38 such that only one optical window 37 at a time may be optically aligned with the optical signal generator 40, and the first and second optical transducers 46 and 26. Such an alignment provides that generally only the fluorescence and bioluminescence signals 145 and 125 emanating from one sample container 35 may be detected by the first and second optical transducers 146 and 126 respectively and that optical signals entering or exiting through the optical window 37 do not impinge on the sample containers 35 in other optical isolation silos 38. FIG. 6 also shows a communications interface 58 electrically coupled to the processor 50. The communications interface 58 may be a serial port, a USB port, or any other interface capable of 2-way communication with the processor 50. The output 150 may be communicated through the communications interface 58 to a remote processor.

Figure 7:
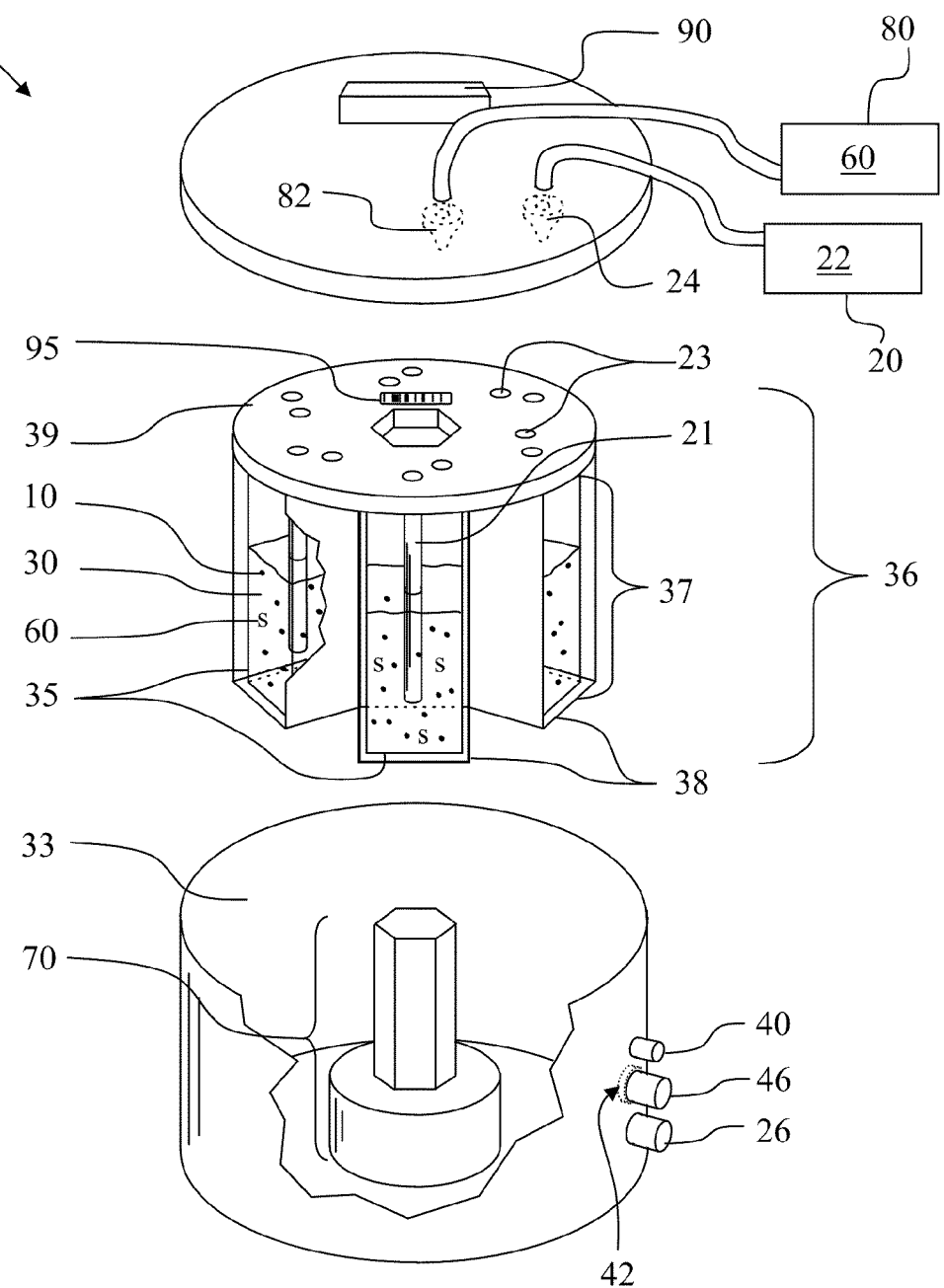
FIG. 7 is an expanded view of an embodiment of the toxicity test system.

FIG. 7 is an expanded view of one embodiment of the toxicity test system 200 further comprising an actuator 70 configured to reposition the cartridge 36 inside the test chamber 33 such that each of the optical windows 37 in turn may be optically aligned with the first and second optical transducers 46 and 26. The actuator 70 may be a servo, a stepper motor, or any other device capable of repositioning the cartridge 36 inside the test chamber 33 such that each of the optical windows 37 in turn may be optically aligned with the first and second optical transducers 46 and 26. As each of the optical windows 37 is optically aligned with the first and second optical transducers 46 and 26, their respective gas tubes 21 are aligned with the first coupling nib 24. Alignment of the gas tube 21 and the first coupling nib 24 allows gas 22 to be introduced into aqueous suspension 30 in the lower end 31 of the aligned sample container 35.

FIG. 7 also shows a bar code 95 affixed to an outer surface of the cartridge cover 39. The bar code 95 may contain cartridge 36 identification information. Also shown is a bar code scanner 90 configured to scan the bar code 95 and to convey cartridge 36 identification information to the processor 50. The bar code scanner 90 need not be mounted to the test chamber 33 as shown in FIG. 7, but may be configured in any way that allows the bar code scanner 90 to scan the bar code 95 whether inside or outside the test chamber 33.

FIG. 7 also shows a test sample distributor 80 configured to distribute an amount of the test sample 60 into each of the sample containers 35. The distributor 80 may be any dosing device capable of dispensing a predetermined amount of test sample 60 into each of the sample containers 35. In one embodiment, the test sample distributor 80 may be coupled to a second coupling nib 82, which may be aligned with the vent 23 of any one of the sample containers 35 to allow an amount of test sample 60 to be distributed to each of the sample containers 35. The processor 50 may control how much test sample 60 is distributed into each sample container 35.

Figure 8:
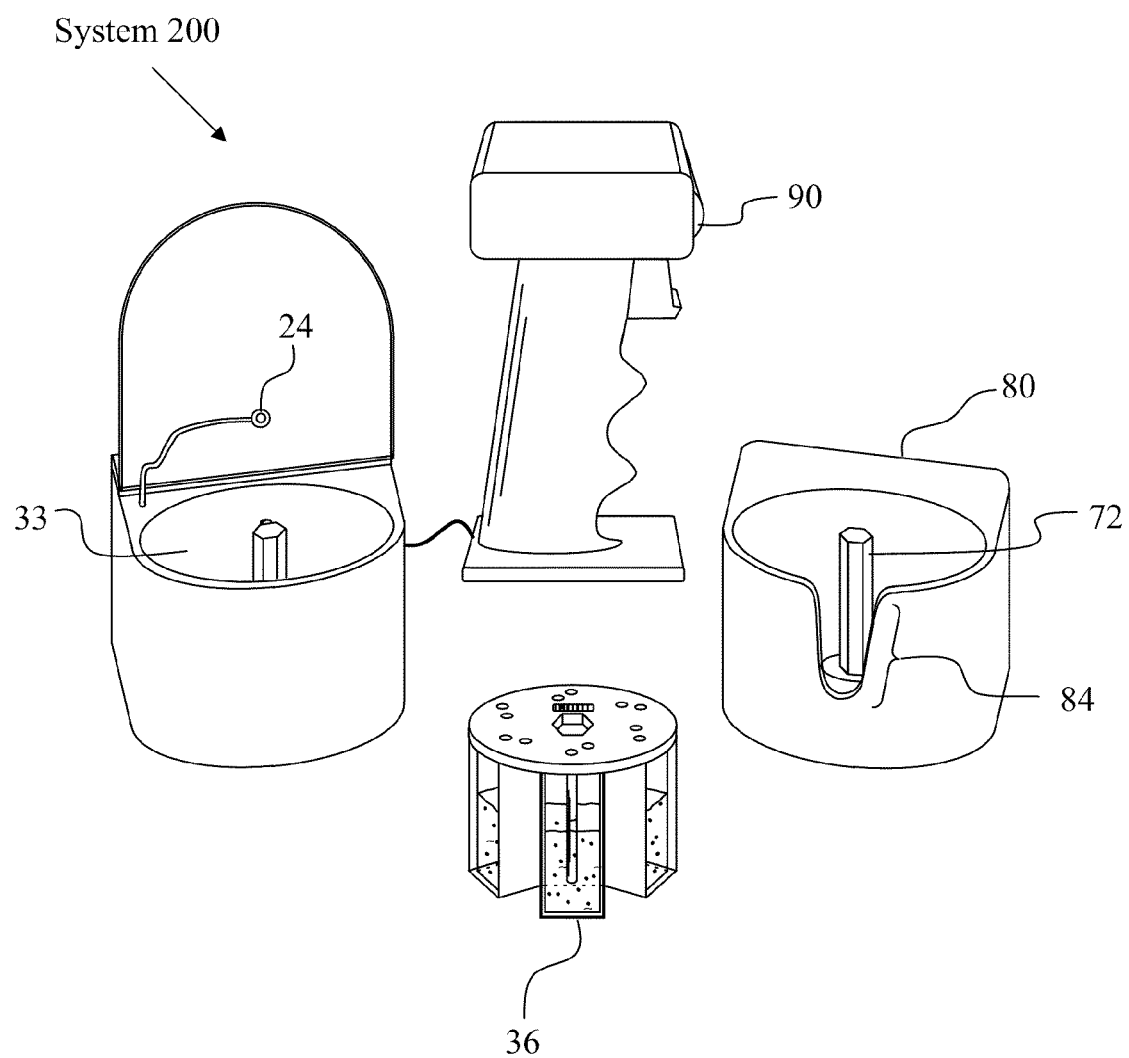
FIG. 8 shows a toxicity test system with a distributor and a bar code scanner.

FIG. 8 shows an alternative embodiment of the toxicity test system 200 wherein the distributor 80 and the bar code scanner 90 are separate from the test chamber 33. In this embodiment, the distributor 80 further comprises a second actuator 72 and a viewing window 84. When the cartridge 36 is placed in the distributor 80, a user may add an amount of the test sample 60 to the sample container 35 that is aligned with the viewing window 84. The second actuator 72 is configured to reposition the cartridge 36 in the distributor 80 such that each sample container 35 in the cartridge 36 may be aligned with the viewing window 84. In the embodiment shown in FIG. 8, the bar code scanner 90 may scan the bar code 95 on the cartridge 36 while the cartridge 36 is outside the test chamber 33.

Figure 9:
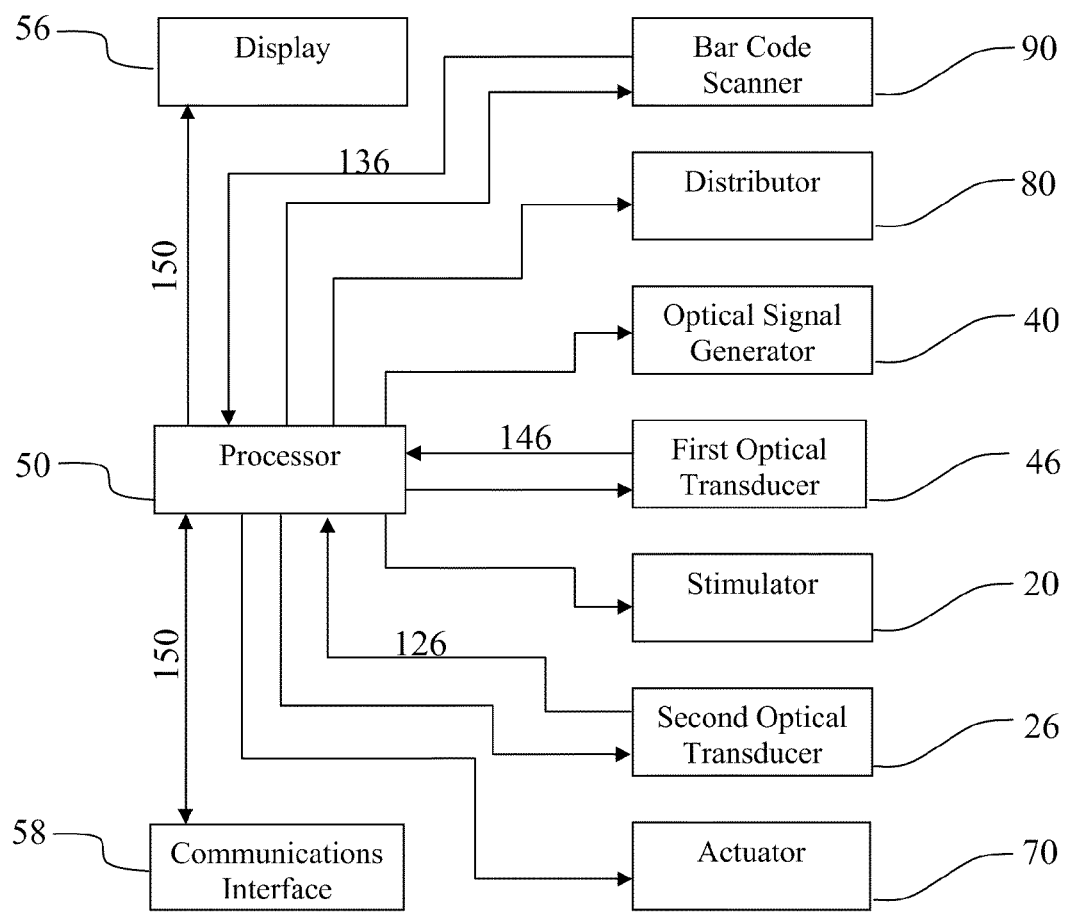
FIG. 9 is a block diagram showing the communication between a processor and other elements of a toxicity test system.

FIG. 9 is a block diagram outlining the communication of the various elements of the toxicity test system 200 with the processor 50. Also shown is an optional display 56, which is capable of displaying the output 150. The display 56 may be any audio, visual, or tactile display capable of conveying information to a user regarding the toxicity of the test sample 60. The display 56 may be operatively coupled to the test chamber 33 or be separate from it.

Figure 10:
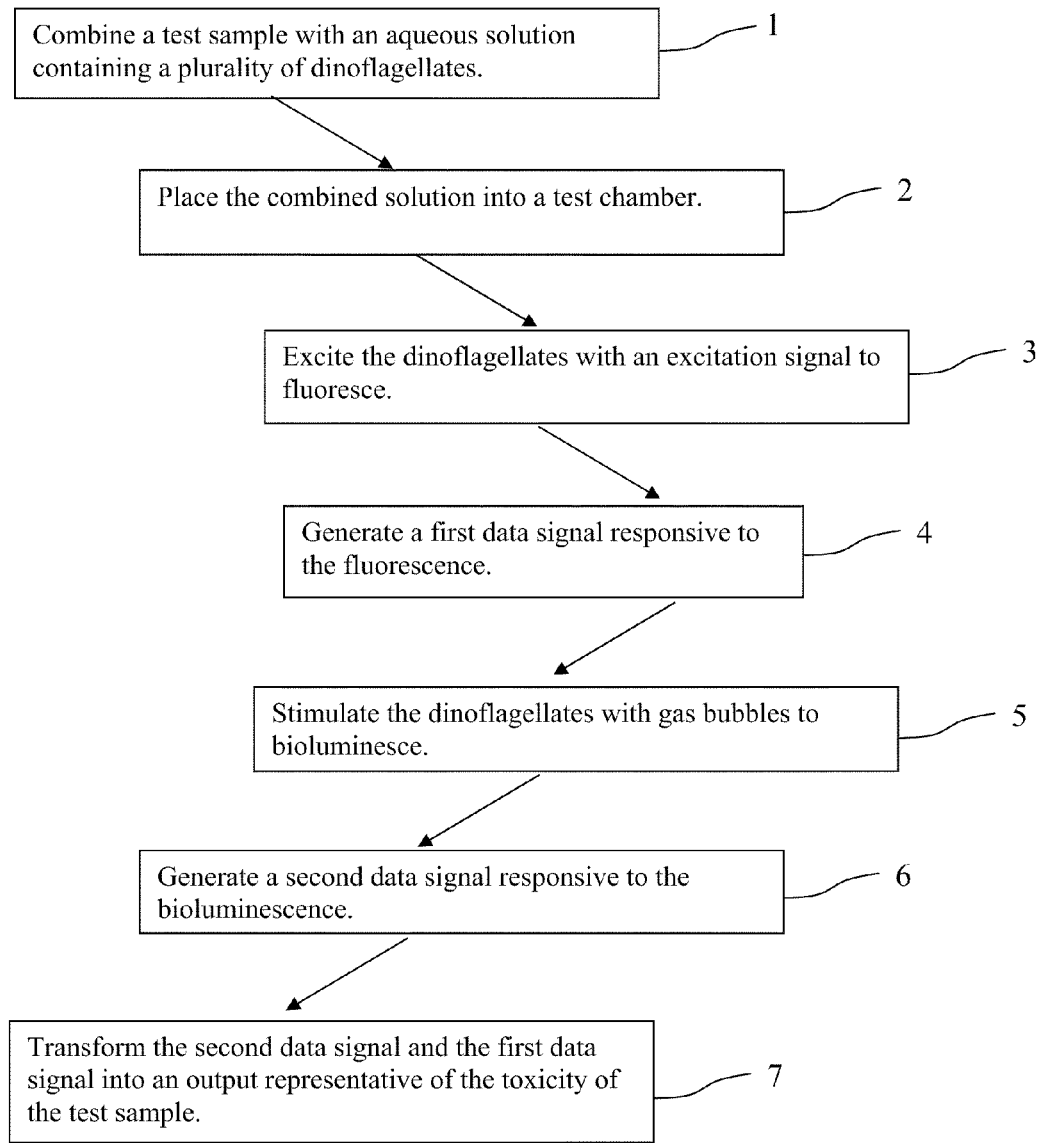
FIG. 10 is a flowchart of a method of using a toxicity test system to measure the toxicity of a test sample.

FIG. 10 illustrates how the toxicity test system 200 may be used to measure the toxicity of a test sample 60. In step one, the test sample 60 is combined with an aqueous suspension 30 containing a plurality of dinoflagellates 10. The combined suspension is then placed into the test chamber 33. Inside the test chamber 33, the dinoflagellates 10 are excited with an excitation signal 140 to fluoresce. In response to the fluorescence signal 145 emitted by the excited dinoflagellates 10, a first data signal 146 is generated. In step five, the dinoflagellates 10 are stimulated with gas 22 bubbles to bioluminesce. In response to the bioluminescence signal 125 emitted by the stimulated dinoflagellates 10, a second data signal 126 is generated. Then the first and second data signals 146 and 126 may be transformed into the output 150 representing the toxicity of the test sample 60.

Figure 11:
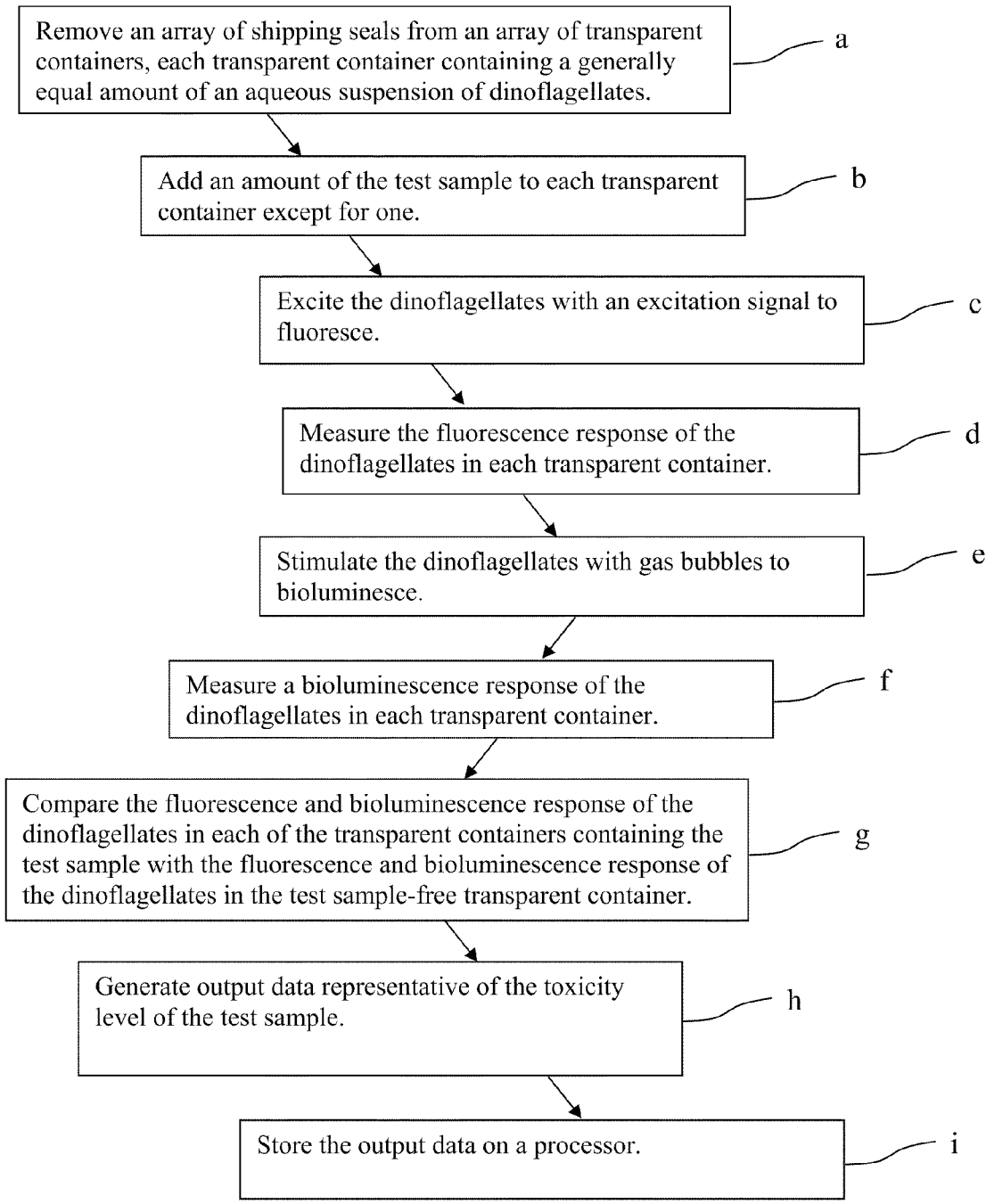
FIG. 11 is another flowchart of a method of using a toxicity test system to measure the toxicity of a test sample.
Figure 12:
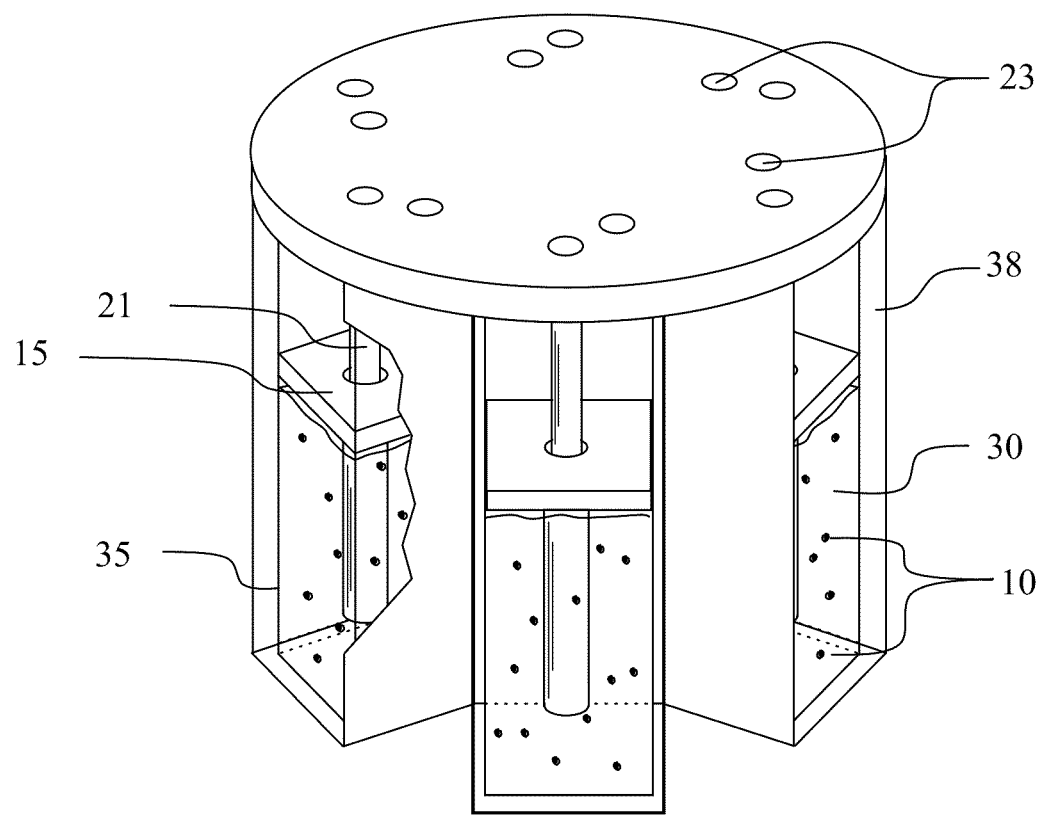
FIG. 12 shows a cartridge with shipping seals.

FIG. 11 illustrates how another embodiment of the toxicity testing system 200 may be used to measure the toxicity of a test sample 60. In step a, an array of shipping seals 15, as shown in FIG. 12 and described below, are removed from an array of sample containers 35. In step b, an amount of the test sample 60 may be added to each sample container 35 except for one. In step c, the dinoflagellates 10 are excited to fluoresce with an excitation signal 140. The fluorescence signal 145 emitted by the dinoflagellates 10 in each sample container 35 in response to the excitation signal 140 is then measured. In step e, the dinoflagellates 10 are stimulated to bioluminesce with gas 22 bubbles. The bioluminescence signal 125 emitted by the dinoflagellates 10 in each sample container 35 in response to the stimulation is then measured. In step g, the fluorescence and bioluminescence responses of the dinoflagellates 10 in each of the sample containers 35 containing the test sample 60 are compared with the fluorescence and bioluminescence responses of the dinoflagellates 10 in the test sample-free sample container 35. An output 150, representing the toxicity of the test sample 60 may then be generated and the output data may also be stored on the processor 50.

FIG. 12 shows the cartridge 36 with shipping seals 15 in place. The shipping seals 15 may be made of any material that is capable of preventing the aqueous suspension 30 from escaping the sample container 35. The shipping seal 15 may be mostly non-reactive with aqueous suspension 30 and the sample container 35. For example, the shipping seal 15 may be made of medical grade silicon. The shipping seal 15 may be any size or shape that is capable of sealing the sample container 35. FIG. 12 shows one embodiment where the shipping seal 15 is an elastomeric plug that may be inserted into each sample container 35 forming a seal. For this embodiment, the size and shape of the shipping seal 15 are such that its insertion into each sample container 35 creates a seal against the inner walls of each sample container 35—preventing the escape of aqueous suspension 30. The shipping seal 15 may enclose the gas tube 21, separating the aqueous suspension 30 from the gas tube 21.

After the bioluminescence and fluorescence responses have been measured for the dinoflagellates 10 in each sample container 35 in a cartridge 36, the cartridge 36 may be discarded and the process repeated with another cartridge 36. The bar code 95 on the cartridge 36 may be scanned with the bar code scanner 90 prior to testing. Also, after scanning and before the bioluminescence and fluorescence responses have been measured, the dinoflagellates 10 may be tested for viability by verifying a fluorescence response from the dinoflagellates 10. The verification of a fluorescence response may be accomplished by exciting the dinoflagellates 10 in the test chamber 33 with an excitation signal 140 and then measuring the fluorescence signal 145 produced by the dinoflagellates 10 in response to the excitation signal 140. After the dinoflagellates 10 have been tested for viability the process described above may begin. If the dinoflagellates 10 were tested and found to be not viable, the same scanning and viability testing procedure may be repeated with a new cartridge 36.

Figure 13:
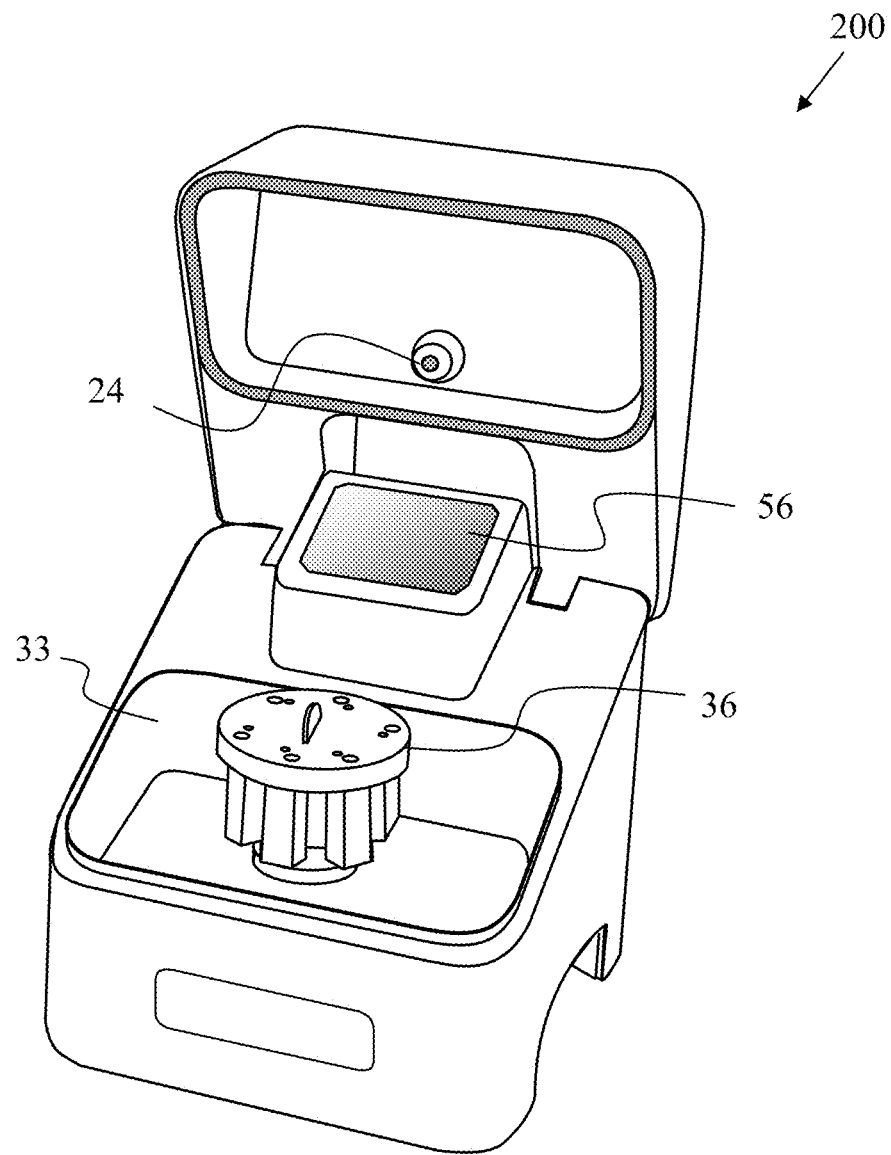
FIG. 13 is a perspective view of a toxicity test system.

FIG. 13 is an illustration of another embodiment of the toxicity test system 200. As shown in FIG. 13, the test chamber 33 can be any desired size and/or shape that suitable for enclosing the cartridge 36. Also shown in FIG. 13 is a depiction of the display 56.

Figure 14:
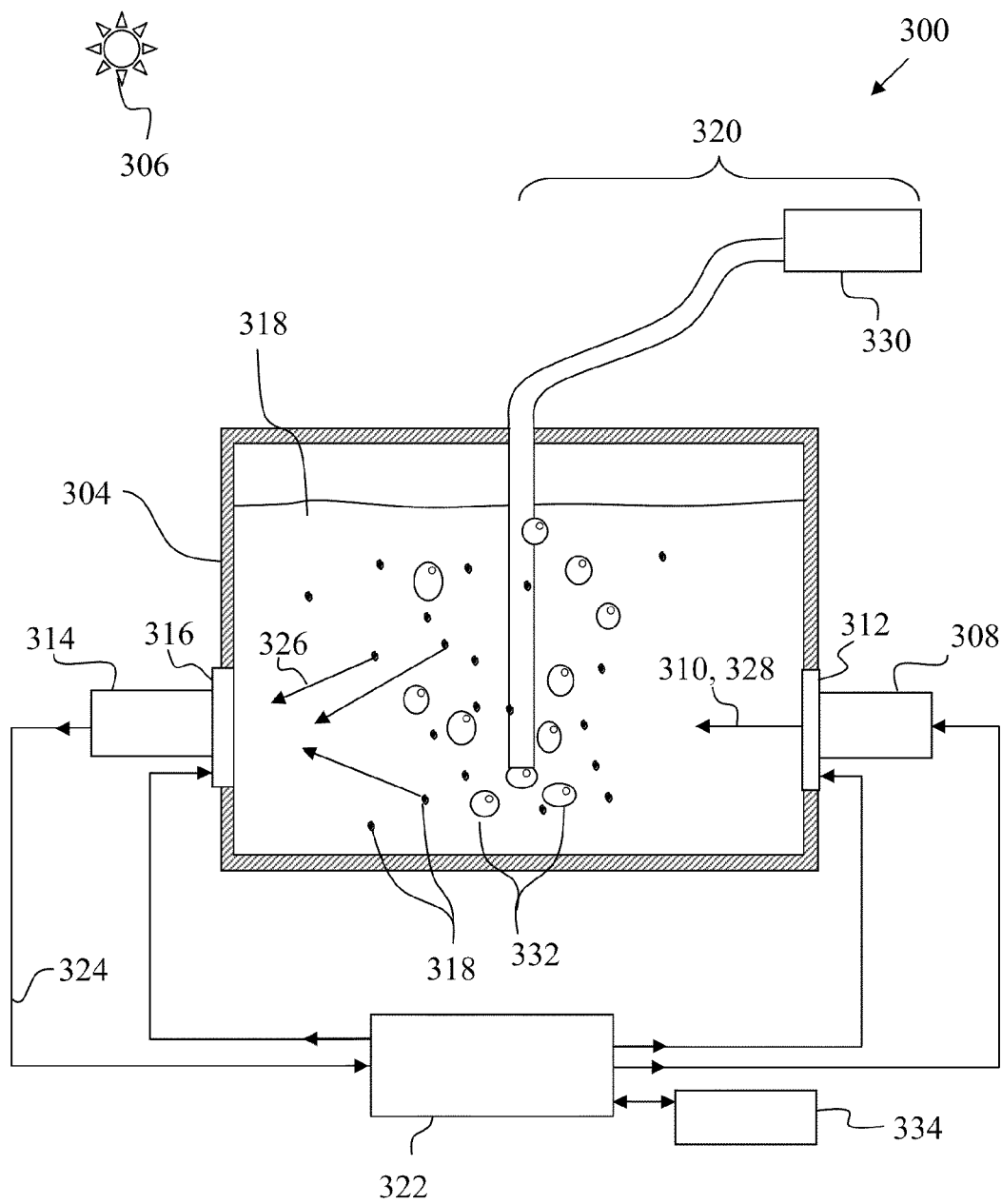
FIG. 14 is a cross-sectional depiction of a system for assessing the characteristics and toxicity of a water sample.

FIG. 14 is a side view of an optical measurement and analysis system 300 for measuring and analyzing the characteristics and toxicity of a water sample 302. As will be described in greater detail herein, the optical measurement and analysis system 300 is a multiple parameter portable optical instrumentation system capable of providing toxicity assessments using bioluminescent dinoflagellates as a biological indicator from packaged kits as well as providing measurements of water characteristics via optical spectroscopy techniques for water (aqueous) samples and sediments. As shown in FIG. 14, the optical measurement and analysis system 300 comprises a light-tight test chamber 304 that is configured to contain the water sample 302. When the water sample 302 is inside the test chamber 304 the water sample 302 is protected from exposure to ambient light 306. The optical measurement and analysis system 300 also comprises an optical signal generator 308 that is configured to emit an optical signal 310 into the test chamber 304. The optical measurement and analysis system 300 also comprises a first digital filter 312, a first optical transducer 314, a second digital filter 316, an aqueous suspension of dinoflagellates 318, a stimulator 320, and a microprocessor 322. The first digital filter 312 is mounted to the test chamber 304 and located between the optical signal generator 308 and the interior of the test chamber 304 such that the first digital filter 312 controls the wavelength of the optical signal 310 entering the test chamber 304.

The first optical transducer 314 is operatively coupled to the microprocessor 322 and disposed to generate a first data signal 324 in response to detecting radiant energy in the test chamber 304. The second digital filter 316 is mounted to the test chamber 304 and located between the first optical transducer 314 and the interior of the test chamber 304 such that the second digital filter 316 controls the wavelength of any radiant energy detected by the first optical transducer 314. The optical signal generator 308, the first optical transducer 314 and the first and second digital filters 312 and 316 respectively are all operatively coupled to the microprocessor 322. The microprocessor 322 may be used to assess the characteristics of the water sample by performing spectrophotometric analyses on the water sample 302 based on the known optical signal 310 and the first data signal 324.

The microprocessor 322 is further configured to assess the toxicity of the water sample 302 by measuring the response of the dinoflagellates 318 to the water sample 302. The aqueous suspension of dinoflagellates 318 may be mixed with the water sample 302 contained in the test chamber 304. The stimulator 320 is disposed to introduce fluid shear stress, as discussed above, thereby stimulating the live dinoflagellates 318 to emit a bioluminescence signal 326. The optical signal generator 308 may also be used to generate an excitation signal 328, which causes the dinoflagellates 318 to fluoresce, which may be detected by the first optical transducer 314.

After the dinoflagellates 318 have been mixed with the water sample 302 the bioluminescence signal 326 and the fluorescence response of the dinoflagellates 318 may be used to determine the toxicity of the water sample 302. The stimulator 320 may be any device capable of introducing fluid shear stress into the water sample 302. In one embodiment, the stimulator 320 is a digitally controlled gas pump 330, controlled by the microprocessor 322 to introduce a variable amount of gas 332 into the water sample 302. If desired, the stimulator 320 may comprise no moving parts, apart from the gas 330, that are in contact with the water sample 302. Accordingly, the microprocessor 322 can be used to vary the flow rate of gas 332 into the water sample 302. For example, a "bubble rate" may be adjusted from "nominal" to "violent." This allows for a highly variable mixing capability to keep the water sample 302 from settling, and/or to ensure that the entire volume is thoroughly presented to the sensing elements for greater accuracy.

The optical measurement and analysis system 300 may further comprise a memory store 334 operatively coupled to the microprocessor 322. The memory store 334 may be any non-transitory computer-readable storage medium internal or external to the microprocessor 322. The memory store 334 is configured to store data representing the toxicity and characteristic assessments of the water sample 302.

Figure 15:
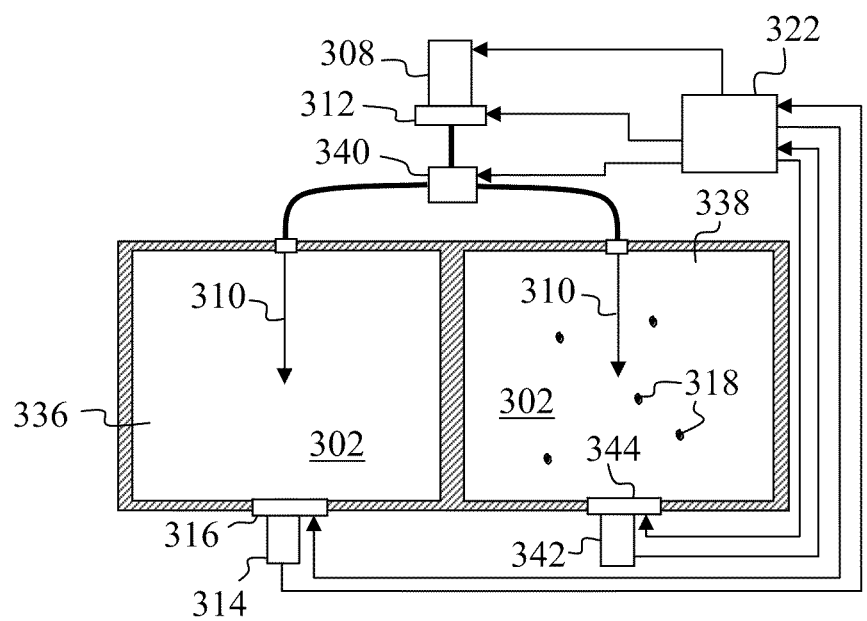
FIG. 15 is a top view of another embodiment of a system for assessing the characteristics and toxicity of a water sample.

FIG. 15 is a top view of an alternative embodiment of the optical measurement and analysis system 300. In the embodiment shown in FIG. 15, the test chamber 304 comprises a first sub-chamber 336 and a second sub-chamber 338, both sub-chambers containing a portion of the water sample 302. The first and second sub-chambers 336 and 338 are optically isolated from each other. The optical signal generator 308 is configured to selectively emit the optical signal 310 into the first sub-chamber 336 and/or the second sub-chamber 338. One way in which the optical signal 310 may selectively be routed to the first sub-chamber 336 and/or the second sub-chamber 338 is by way of an optical splitter 340, but any suitable means of routing the optical signal 310 may be employed. As shown in FIG. 15, the first optical transducer 314 and the second digital filter 316 are optically coupled only to the first sub-chamber 336. Also depicted in FIG. 15 are a second optical transducer 342 and a third digital filter 344. The second optical transducer 342 is operatively coupled to the microprocessor 322 and is configured to detect radiant energy within the second sub-chamber 338. The third digital filter 344 is operatively coupled to the microprocessor 322 and is situated between the second sub-chamber 338 and the second optical transducer 342 such that the third digital filter 344 controls the wavelength of light that is detected by the second optical transducer 344. The first sub-chamber 336 is configured to be used for spectrophotometric analysis of the water sample 302. The second sub-chamber 338 also contains the aqueous suspension of dinoflagellates 318 and is configured to be used for assessing the toxicity of the water sample 302. While not shown in FIG. 15 for ease of viewing, the stimulator 320 is also operatively coupled to the second sub-chamber 338 such that it can agitate and stimulate the dinoflagellates 318.

Figure 16:
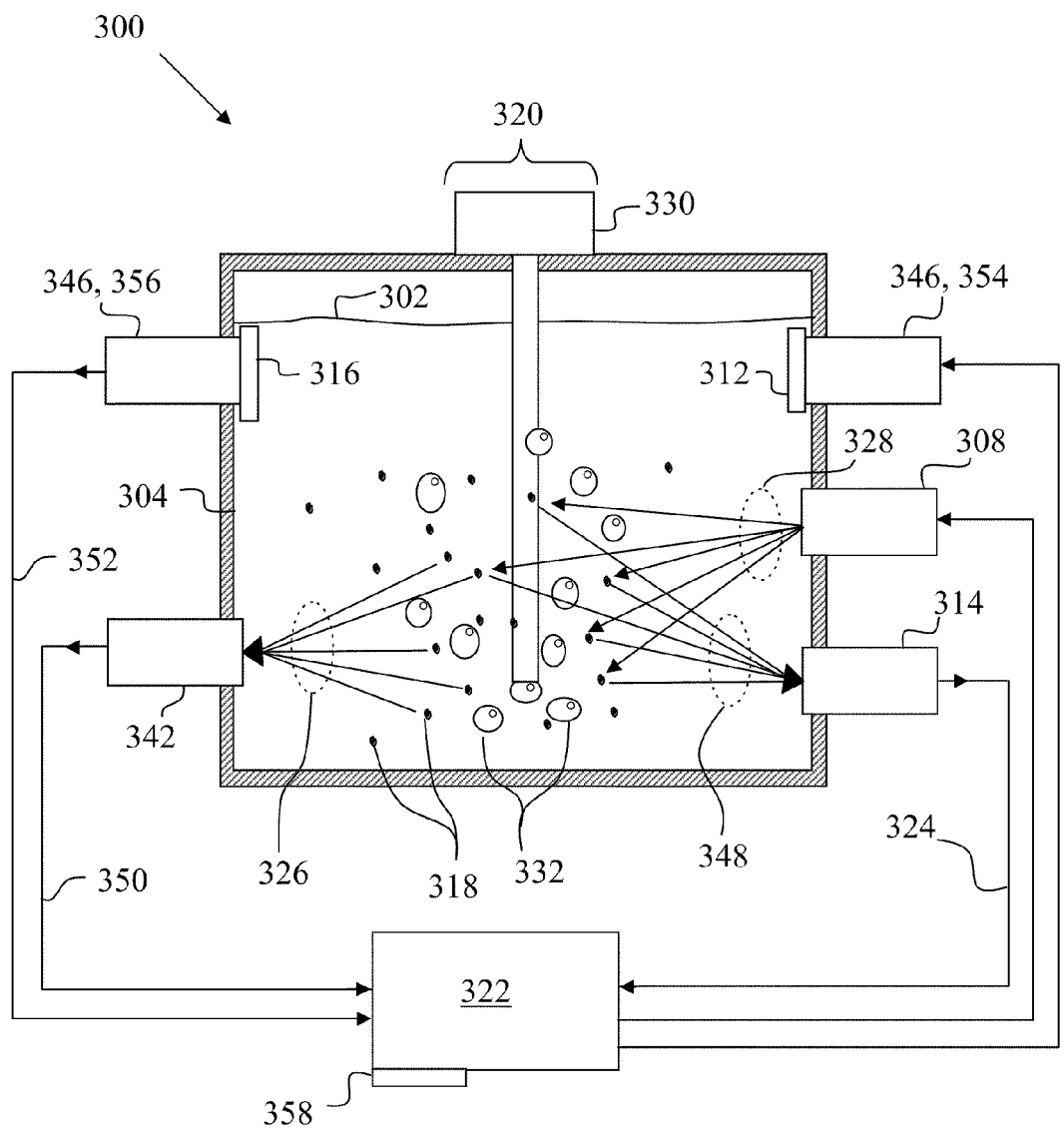
FIG. 16 is a cross-sectional depiction of another embodiment of a system for assessing the characteristics and toxicity of a water sample.

FIG. 16 is a side view of another embodiment of the optical measurement and analysis system 300 that may be used for measuring and analyzing the properties of the water sample 302. This embodiment is similar to the toxicity test system 200 depicted in FIG. 1 with the addition of a spectrophotometer 346. In this embodiment, the dinoflagellates 318 emit a fluorescence signal 348 in response to the excitation signal 328 produced by the optical signal generator 308, and the second optical transducer 342 generates a second data signal in response to detecting the fluorescence signal 348. The spectrophotometer 346 is operatively coupled to the test chamber 304 and the microprocessor 322 and is configured to generate a third data signal 352 that represents an optical characteristic of the water sample 302. In this embodiment, the spectrophotometer 346 comprises a second optical signal generator 354 and a third optical transducer 356. The microprocessor 322 is disposed to receive the first, second, and third data signals 324, 350, and 352. In addition, the spectrophotometer may optionally comprise the variable-wavelength, first digital filter 312 optically coupled between the test chamber 304 and the second optical signal generator 354. The spectrophotometer may also optionally comprise the variable-wavelength, second digital filter 316 optically coupled between the test chamber 304 and the third optical transducer 356. FIG. 16 also shows a communications port 358 operatively coupled to the microprocessor 322. The communications interface 358 may be any communication interface capable of transferring data and power to/from the microprocessor 322. A suitable example of the communications interface 358 is a universal serial bus (USB) interface.

Figure 17:
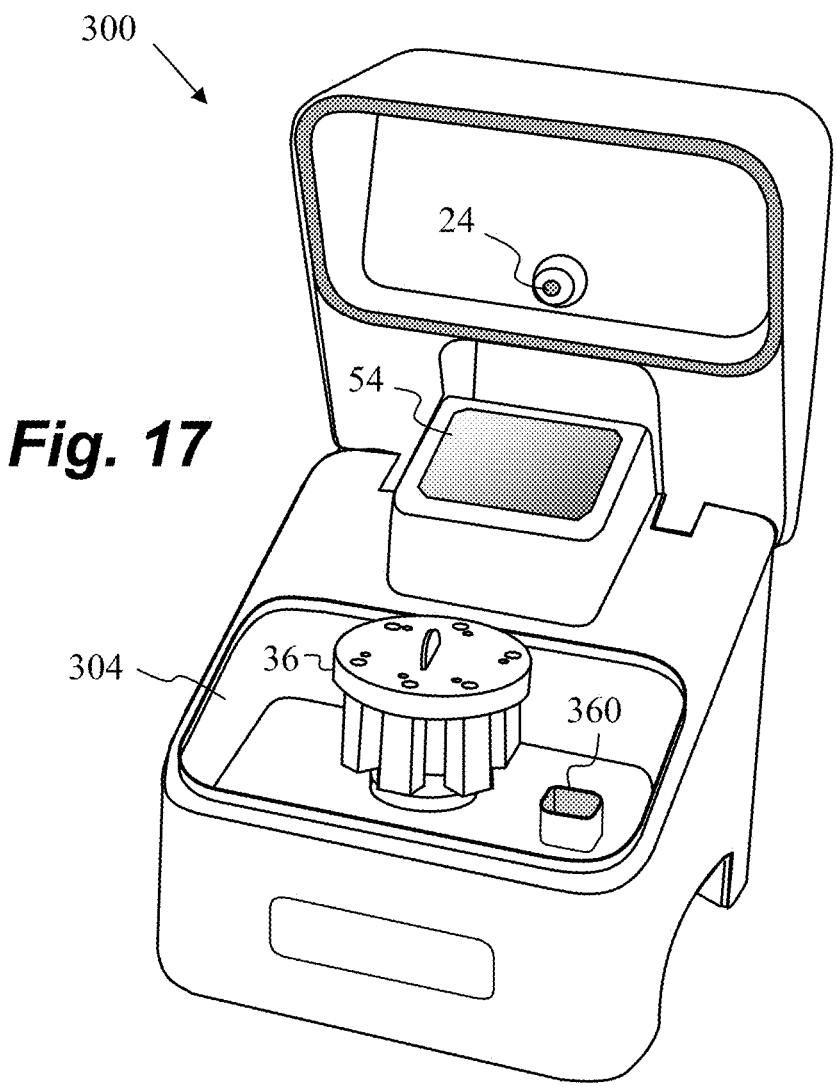
FIG. 17 is a perspective view of another embodiment of a system for assessing the characteristics and toxicity of a water sample.

FIG. 17 is a perspective view of one embodiment of the optical measurement and analysis system 300. This embodiment is similar to the toxicity test system 200 portrayed in FIG. 13, but with the addition of a spectrophotometry slot 360. In this embodiment, the spectophotometry slot 360 is part of the second sub-chamber 338, in which a portion of the water sample 302 may be placed to conduct light spectrum analyses.

Figure 18:
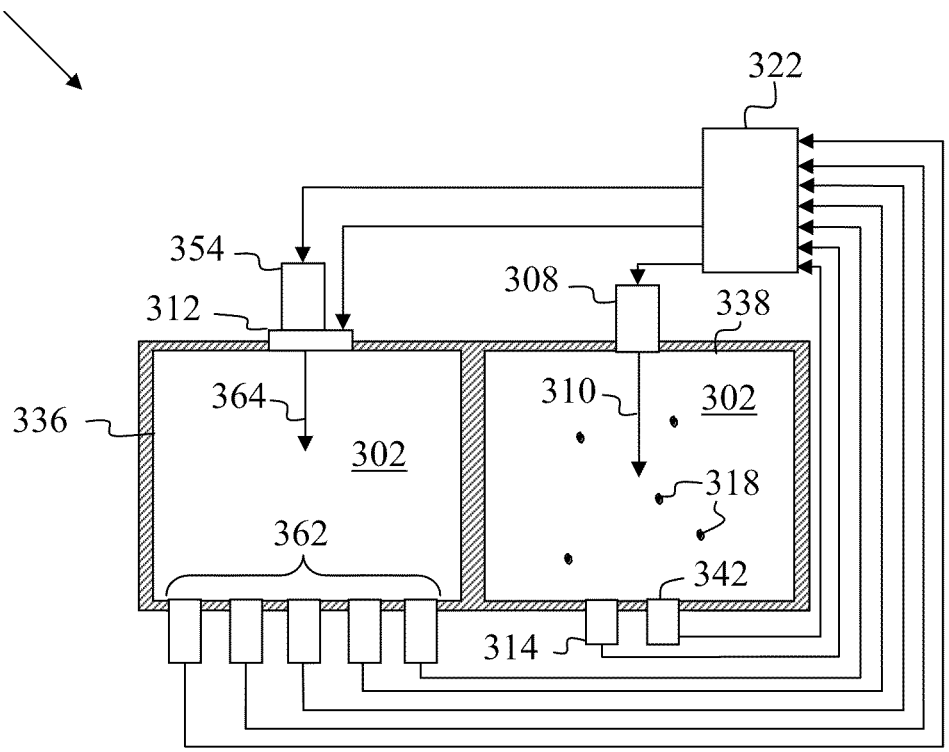
FIG. 18 is a top view of another embodiment of a system for assessing the characteristics and toxicity of a water sample.

FIG. 18 is a top view of another embodiment of the optical measurement and analysis system 300 comprising a plurality of wavelength-specific optical transducers 362. Each of the plurality of wavelength-specific optical transducers 362 is configured to detect light having a different wavelength. Although there are five wavelength-specific optical transducers 362 shown in FIG. 18, it is to be understood that there may be any desired number of wavelength-specific optical transducers 362.

From the above description of System for Measuring and Analyzing Properties of Water and Sediment Samples, it is manifest that various techniques may be used for implementing the concepts of the claimed invention without departing from the scope of the claims. The described embodiments are to be considered in all respects as illustrative and not restrictive. It should also be understood that optical measurement and analysis system is not limited to the particular embodiments described herein, but is capable of many embodiments without departing from the scope of the claims.

We claim:

1. A system for assessing the characteristics and toxicity of a water sample comprising:

a light-tight test chamber disposed to contain the water sample;

an optical signal generator configured to emit an optical signal into the test chamber;

a first digital filter disposed between the optical signal generator and the test chamber such that the first digital filter controls the wavelength of the optical signal that enters the test chamber;

a first optical transducer disposed to generate a first data signal in response to detecting radiant energy in the test chamber;

a second digital filter disposed between the first optical transducer and the test chamber such that the second digital filter controls the wavelength of the radiant energy that is detected by the first optical transducer;

an aqueous suspension of live dinoflagellates contained within the test chamber and mixed with the water sample;

a stimulator disposed to stimulate the live dinoflagellates to emit a bioluminescence signal; and a microprocessor operatively coupled to the optical signal generator, the first digital optical filter, the stimulator, the first optical transducer, and the second digital filter, wherein the microprocessor is configured to assess the characteristics of the water sample through spectral analysis based on the first data signal, and wherein the microprocessor is further configured to assess the toxicity of the water sample based on the bioluminescence signal and a fluorescence response of the dinoflagellates to an excitation signal from the optical signal generator.

2. The system of claim 1, where in the stimulator is digitally controlled by the microprocessor and configured to introduce a variable amount of gas into the combination of the aqueous suspension of dinoflagellates and the water sample, wherein the stimulator comprises no moving parts, apart from the gas, that are in contact with the water sample.

3. The system of claim 2, further comprising a memory store operatively coupled to the microprocessor, wherein the memory store is configured to store data representing the toxicity and characteristic assessments of the water sample.

4. The system of claim 2, wherein the test chamber comprises first and second sub-chambers that are optically isolated from each other, wherein the optical signal generator is configured to selectively emit the optical signal into the first sub-chamber and/or the second sub-chamber, and wherein the first optical transducer and the second digital filter are optically coupled only to the first sub-chamber, and wherein the system of claim 2 further comprises:

a second optical transducer operatively coupled to the microprocessor and configured to detect light within the second sub-chamber;

a third digital filter operatively coupled to the microprocessor and disposed between the second sub-chamber and the second optical transducer such that the third digital filter controls the wavelength of light that is detected by the second optical transducer; and wherein a first portion of the water sample is contained in the first sub-chamber and a second portion of the water sample together with the aqueous suspension of dinoflagellates is contained in the second sub-chamber.

5. A system for measuring and analyzing the properties of a water sample comprising:

an aqueous suspension of dinoflagellates;

a light-tight test chamber configured to contain the aqueous suspension of dinoflagellates and the water sample;

an optical signal generator configured to emit an excitation signal, the excitation signal disposed to excite the dinoflagellates to emit a fluorescence signal if the dinoflagellates are alive;

a first optical transducer configured to produce a first data signal in response to detecting the fluorescence signal;

a stimulator configured to introduce a gas into the water sample, wherein the stimulator comprises no moving parts, apart from the gas, that are in contact with the water sample, wherein the gas is disposed to stimulate the dinoflagellates to emit a bioluminescence signal if the dinoflagellates are alive;

a second optical transducer configured to produce a second data signal in response to detecting the bioluminescence signal;

a spectrophotometer operatively coupled to the test chamber and configured to generate a third data signal representative of optical characteristics of the water sample; and a microprocessor disposed to receive the first, second, and third data signals.

6. The system of claim 5, wherein the spectrophotometer comprises:

a second optical signal generator optically coupled to the test chamber and operatively coupled to the microprocessor;

a third optical transducer configured to generate and send the third data signal to the microprocessor upon detecting radiant energy in the test chamber; and a variable-wavelength, first digital filter optically coupled between the test chamber and the third optical transducer, wherein the first digital filter is operatively coupled to the microprocessor such that the microprocessor controls the wavelength of light that is filtered by the first digital filter.

7. The system of claim 6, further comprising a memory store operatively coupled to the microprocessor and configured to store the first, second, and third data signals corresponding to the water sample.

8. The system of claim 6, wherein the spectrophotometer further comprises a variable-wavelength, second digital filter optically coupled between the test chamber and the second optical signal generator, wherein the second digital filter is operatively coupled to the microprocessor such that the microprocessor controls the wavelength of light from the second optical signal generator that enters the test chamber.

9. The system of claim 8, further comprising a universal serial bus (USB) interface electrically connected to the microprocessor.

10. The system of claim 8, further comprising a cartridge configured to be supported inside the test chamber, the cartridge comprising an array of transparent sample containers, each transparent sample container containing a generally equal amount of the aqueous suspension of dinoflagellates and the water sample.

11. The system of claim 10, wherein the cartridge further comprises an array of optical isolation silos configured to optically isolate the transparent sample containers from each other, and wherein each optical isolation silo comprises an optical window through which the excitation signal, the fluorescence signal and the bioluminescence signal may pass.

12. The system of claim 11, wherein only one optical window is optically aligned with the first and second optical transducers and the spectrophotometer at a time such that approximately only radiant energy emanating from one sample container at a time may be detected by the first, second, and third optical transducers.

13. The system of claim 12, further comprising an actuator configured to reposition the cartridge such that each of the optical windows in turn may be optically aligned with the first and second optical transducers and the spectrophotometer.

14. An apparatus for testing a water sample comprising:

a first light-tight test chamber configured to hold a first portion of the water sample;

an aqueous suspension of dinoflagellates mixed with the water sample in the first test chamber;

a first optical signal generator configured to emit a first optical signal, the first optical signal disposed to excite the dinoflagellates to emit a fluorescence signal if the dinoflagellates are alive;

a first optical transducer configured to produce a first data signal in response to detecting the fluorescence signal in the first test chamber;

a stimulator configured to introduce a gas into the first portion of the water sample, wherein the stimulator comprises no moving parts, apart from the gas, that are in contact with the first portion of the water sample, wherein the gas is disposed to stimulate the dinoflagellates to emit a bioluminescence signal if the dinoflagellates are alive;

a second optical transducer configured to produce a second data signal in response to detecting the bioluminescence signal in the first test chamber;

a microprocessor configured receive the first and second data signals and to compare the first and second data signals to a control data to generate an output representing the toxicity of the water sample;

a second light-tight test chamber configured to hold a second portion of the water sample;

a second optical signal generator mounted to the second test chamber and operatively coupled to the microprocessor, wherein the second optical signal generator is disposed to emit a second optical signal into the second portion of the water sample contained in the second test chamber; and a third optical transducer disposed to send a third data signal to the microprocessor upon detecting light in the second test chamber, wherein the microprocessor is further configured to assess the characteristics of the water sample based on the third data signal.

15. The water sample testing apparatus of claim 14, further comprising a first variable-wavelength digital filter operatively coupled to the microprocessor and disposed between the second optical signal generator and the second test chamber such that the microprocessor is configured to control the wavelength of the second optical signal that enters the second test chamber.

16. The water sample testing apparatus of claim 15, further comprising a second variable-wavelength digital filter operatively coupled to the microprocessor and disposed between the third optical transducer and the second test chamber such that the microprocessor is configured to control the wavelength of light that may be detected by the third optical transducer.

17. The water sample testing apparatus of claim 16, wherein the stimulator comprises a digitally-controlled pump that is operatively coupled to the microprocessor such that the microprocessor can adjust a rate of gas introduction into the first test chamber.

18. The water sample testing apparatus of claim 15, further comprising a plurality of wavelength-specific optical transducers, each disposed to send a corresponding data signal to the microprocessor upon detecting light in the second test chamber, wherein each of the plurality of wavelength-specific optical transducers is configured to detect light having a different wavelength.

19. The water sample testing apparatus of claim 17, further comprising a memory store operatively coupled to the microprocessor, wherein the memory store is configured to store the toxicity and characteristic assessment of the water sample.

20. The water sample testing apparatus of claim 19, further comprising a universal serial bus (USB) interface operatively coupled to the microprocessor such that power for the water sample testing apparatus may be delivered through the USB interface.

* * * * *